(12) United States Patent
Sundermann et al.

(10) Patent No.: US 7,011,967 B1
(45) Date of Patent: Mar. 14, 2006

(54) SERIPANCRIN

(75) Inventors: Britta Sundermann, Darmstadt (DE); Uwe Hofmann, Alsbach (DE); Siegfried Matzku, Zwingenberg (DE); Oliver Wilbert, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 644 days.

(21) Appl. No.: 10/030,688

(22) PCT Filed: Jul. 4, 2000

(86) PCT No.: PCT/EP00/06211

§ 371 (c)(1), (2), (4) Date: Jan. 14, 2002

(87) PCT Pub. No.: WO01/04141

PCT Pub. Date: Jan. 18, 2001

(30) Foreign Application Priority Data

Jul. 12, 1999 (EP) .......................................... 99113428

(51) Int. Cl.
*C12N 9/64* (2006.01)

(52) U.S. Cl. ..................... 435/226; 435/7.1; 435/69.1; 435/252.3; 435/320.1; 435/325; 514/12; 530/350; 536/23.2; 536/23.4; 536/23.5

(58) Field of Classification Search ................ 435/7.1, 435/69.1, 226, 252.3, 320.1; 514/12; 530/350; 536/23.2

See application file for complete search history.

(56) References Cited

U.S. PATENT DOCUMENTS

| | | | | |
|---|---|---|---|---|
| 5,116,964 | A | * | 5/1992 | Capon et al. ............... 536/23.5 |
| 6,203,979 | B1 | * | 3/2001 | Bandman et al. ............... 435/6 |
| 6,432,690 | B1 | | 8/2002 | Xu et al. |
| 6,573,068 | B1 | | 6/2003 | Milne Edwards et al. |
| 6,649,741 | B1 | | 11/2003 | O'Brien et al. |
| 6,670,463 | B1 | | 12/2003 | Mitcham et al. |

FOREIGN PATENT DOCUMENTS

| | | | |
|---|---|---|---|
| JP | 09149790 | | 6/1997 |
| WO | WO 94/01548 | * | 1/1994 |
| WO | WO 9936550 | | 7/1999 |
| WO | WO 0012708 | | 3/2000 |
| WO | WO 0012758 | | 3/2000 |

OTHER PUBLICATIONS

Wells, J.A. (1990). Additivity of mutational effects in proteins. Biochemistry 29:8509–8517.*

Ngo et al. (1990). Computational complexity, protein structure prediction, and the Levinthal paradox. In Merz and Le Grand (Eds.) The Protein Folding Problem and Tertiary Structure Prediction. Birkhauser:Boston.*

Szabo et al. (2003). Type II transmembrane serine proteases. Thrombosis and Haemostasis 90:185–193.*

Gress et al. (1997). Identification of genes with specific expression in pancreatic cancer by cDNA representational difference analysis. Genes, Chromosomes and Cancer 19:97–103.*

Paoloni–Giacobino A et al., "Cloning of the TMPRSS2 gene, which encodes a novel serine protease with transmembrane, LDLRA, and SRCR domains and maps to 21Q22.3," Genomics, Sep. 15, 1997, pp. 309–320, vol. 44, No. 3, XP000856785, ISSN: 0888-7543, Academic Press, San Diego, US, cited in the application, the whole document.

* cited by examiner

*Primary Examiner*—Lorraine Spector
*Assistant Examiner*—Jon M. Lockard
(74) *Attorney, Agent, or Firm*—Millen, White, Zelano & Branigan, P.C.

(57) ABSTRACT

Seripancrin polypeptides and polynucleotides and methods for producing such polypeptides by recombinant techniques are disclosed. Also disclosed are methods for utilizing Seripancrin polypeptides and polynucleotides in diagnostic assays.

16 Claims, No Drawings

SERIPANCRIN

FIELD OF THE INVENTION

This invention relates to newly identified polypeptides and polynucleotides encoding such polypeptides sometimes hereinafter referred to as "Seripancrin", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to Seripancrin, in particular Seripancrin polypeptides and Seripancrin polynucleotides, recombinant materials and methods for their production. Such polypeptides and polynucleotides are of interest in relation to methods of treatment of certain diseases, including, but not limited to, cancer,osteoporosis, aberrant wound healing, angiogenesis, inflammatory disorders, chronic obstructive pulmonary disorder, diabetes, arthritis, stroke and cardiovascular diseases, hereinafter referred to as "diseases of the invention". In a further aspect, the invention relates to methods for identifying agonists and antagonists (e.g., inhibitors) using the materials provided by the invention, and treating conditions associated with Seripancrin imbalance with the identified compounds. In a still further aspect. The invention relates to diagnostic assays for detecting diseases associated with inappropriate Seripancrin activity or levels.

DESCRIPTION OF THE INVENTION

In a first aspect, the present invention relates to Seripancrin polypeptides. Such polypeptides include:
(a) an isolated polypeptide encoded by a polynucleotide comprising the sequence selected from SEQ ID NO:1;
(b) an isolated polypeptide comprising a polypeptide sequence having at least 95%, 96%, 97%, 98%, or 99% identity to the polypeptide sequence selected from SEQ ID NO:2;
(c) an isolated polypeptide comprising the polypeptide sequence selected from SEQ ID NO:2;
(d) an isolated polypeptide having at least 95%, 96%, 97%, 98%, or 99% identity to the polypeptide sequence from SEQ ID NO:2;
(e) the polypeptide sequence selected from SEQ ID NO:2; and
(f) an isolated polypeptide having or comprising a polypeptide sequence that has an Identity index of 0.95, 0.96, 0.97, 0.98, or 0.99 compared to the polypeptide sequence selected from SEQ ID NO:2;
(g) fragments and variants of such polypeptides in (a) to (f).

Polypeptides of the present invention are believed to be members of the serine protease family of polypeptides. Cell proliferation and tissue growth under normal conditions are tightly regulated processes. An intricate system of extracellular and intracellular signalling pathways makes sure that the proliferating cells are not infiltrating into surrounding tissues. Circumventing this control is the hallmark of malignant tumours. It is this contribution to the metastatic property of malignant tumours, which is largely responsible for their lethality (Stetler-Stevenson, W. G. et al., Annu. Rev. Cell Biol. 1993; 9:541–73; Meyer, T. and Hart, I. R., Eur. J Cancer 1998; 34(2):214–21).

Metastasis is a multistage process involving numerous aberrant functions of tumour cells. These include tumour angiogenesis, attachment, adhesion to the vascular basement membrane, local proteolysis, degradation of extracellular matrix components, migration through the vasculature, invasion of the basement membrane, and proliferation at secondary sites (Poste, G. and Fidler, I. J., Nature 1980; 283: 139–146; Liotta, L. A. et al., Cell 1991; 64(2):327–336). Increased proteolytic activity is one documented feature of metastatisizing cells. This increased activity is thought to result from the combined aberrant regulation of extracellular proteolytic enzymes (Chen, W. T.; Curr. Opin. Cell Biol. 1992; 4(5): 802–809) in cancer cells as well as in the surrounding stroma.

At the cell-extracellular matrix interface, tumour cells elaborate membrane protrusions termed 'invadopodia' that exhibit increased proteolytic activities at invasion foci and thus allow metastatic cells to digest the surrounding matrix (Chen, W. T., Enzyme Protein 1996; 49:59–71). Perhaps the so far best understood example of such membrane associated protease activity is the involvement of urokinase plasminogen activator and matrix metalloproteinases in some cases of tumour cell migration (DeClerk, Y. A. and Laug, W. E., Enzyme Protein 1996; 49:72–84). Interestingly, it has also been shown that these proteins facilitate the sprouting of blood vessels to feed the growing tumour. (Kroon, M. E. et al., Am. J Pathol. 1999;154(6):1731–42; Rabbani, S. A., In Vivo 1998;12(1):135–42). Accordingly, in animal models it has already been shown that interfering with these proteolytic mechanisms is a valid approach to treat metastasizing tumours (Wilson, C. L. et al., Proc. Natl Acad. Sci. USA 1997; 94:1402–1407).

Disclosed herein is the identification of a novel extracellular serine protease (reviewed in Rawlings, N. D. and Barrett, A. J.; Methods Enzymol. 1994: 244:19–61), Seripancrin, specifically over-expressed in certain kinds of tumours, like (but not limited to) colon cancer, ovarian cancer, pancreas cancer, prostate cancer and uterine cancer, or in stromal cells in close proximity to these tumour cells. This protease is a typical type II transmembrane domain protein with a short cytoplasmic N-terminus which could interact with intracellular components of the cytoskeleton and/or intracellular signalling or degradation pathways. Adjacent to that is a transmembrane domain, immediately followed by a low density lipoprotein (LDL) domain, a scavenger receptor cysteine-rich (SRCR) domain and a protease domain, which based on its sequence homology identifies this protein as a new member of the class of trypsin-like serine proteases. This domain structure is shared between Seripancrin and its so far closest homologue, the recently cloned type II transmembrane-anchored serine protease TMPRSS2 (Paoloni-Giacobino, A. et al., Genomics 1997; 44(3):309–320). The LDL domain, originally identified as seven tandemly repeated modules in the low density lipoprotein receptor (Sudhof, T. C. et al., Science 1985; 228:815–822), is known to contain a calcium binding domain and mediates binding to lipoproteins (Deborah F. et al., Nature 1997; 388:691–693; Russell, D. WQ. et al., J Biol. Chem. 1989; 264:21688–21782). Similarly, the SRCR domain, originally identified during the analysis of type I macrophage scavenger receptor (Freeman, M. et al., Proc. Natl Acad. Sci. USA 1990: 87:8810–8814). is thought to mediate protein-protein interactions and ligand binding (Hohenester, E. et al., Nat. Struct. Biol. 1999; 6(3): 228–232).

This modular structure of Seripancrin suggests that it is a transmembrane serine protease where the LDL and SRCR domains help to define the specificity of Seripancrin's intra- and intermolecular interactions. Although not yet shown. Seripancrin might be expressed in an inactive form which then has to be activated first (most likely by a proteolytic mechanism) to become proteolytically active. However, it is also conceivable that the protease inactive form alone can already perform important protein-protein interactions, similar to so-called adaptor proteins which also lack any enzymatic activities. This possibility is supported by the fact that expression of a differentially spliced isoform can be detected for Seripancrin which lacks the proteolytic domain (as well as the SRCR domain). Additionally, cleavage of Seripancrin can result in a secreted form which could function in distance to the Seripancrin expressing cell. Beside these two so far described isoforms there is a third splicing isoform detectable, which represents basically the ORF of the main splicing isoform (AA1432) plus an additional stretch of 60 amino acids with no obvious sequence homology added at the C-terminus.

Cloning starting point was the identification of a short stretch of cDNA which is overexpressed in pancreas tumour (U54603; Gress, T. M. et al., Genes Chromosomes Cancer 1997; 19(2):97–103). The authors did not disclose any homology for this transcript. Extending this sequence (using standard molecular and biochemical methods) resulted in the identification of the full length form as well as a truncated isoform of this gene which we called Seripancrin. The fact that this gene seems to be specifically upregulated in various cancers, whereas its expression is low up to not detectable in the corresponding healthy tissues, implies that Seripancrin could not only represent a good marker for cancerous tissues, but it could also represent a novel drug target to treat specifically primary and secondary tumours. The gene encoding Seripancrin maps to chromosome 11q22-q23, a locus known to contain cell proliferation and metastasis promoting genes. Interestingly, a cluster of matrix metalloproteases (including MMP-1, MMP-3 and MMP-10; Formstone, C. J. et al., Genomics 1993; 16:289–291) has also been mapped to that region, which could suggest that if there is a correlation between locus and epistatic interaction, Seripancrin is activating or is being activated by any of these MMPs (something similar has been shown for the serine proteases plasmin and trypsin, which have been implicated in the activation of pro-MMP-1 and pro-MMP-3 (Rao C. N. et al., Biochem. Biophys. Res. Commun. 1999; 255(1): 94–98 and references therein)).

The biological properties of the Seripancrin are hereinafter referred to as "biological activity of Seripancrin" or "Seripancrin activity". Preferably, a polypeptide of the present invention exhibits at least one biological activity of Seripancrin.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of Seripancrin, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occuring sources, from genetically engineered host cells comprising expression systems (vide infra) or by chemical synthesis, using for instance automated peptide synthesisers, or a combination of such methods.. Means for preparing such polypeptides are well understood in the art.

In a further aspect, the present inventions relates to Seripancrin polynucleotides. Such polynucleotides include:

(a) an isolated polynucleotide comprising a polynucleotide sequence having at least 95%, 96%, 97%, 98%, or 99% identity to the polynucleotide sequence selected from SEQ ID NO:1;

(b) an isolated polynucleotide comprising the polynucleotide selected from SEQ ID NO:1;

(c) an isolated polynucleotide having at least 95%. 96%, 97%, 98%, or 99% identity to the polynucleotide selected from SEQ ID NO:1;

(d) the isolated polynucleotide selected from SEQ ID NO:1;

(e) an isolated polynucleotide comprising a polynucleotide sequence encoding a polypeptide sequence having at least 95%, 96%, 97%, 98%, or 99% identity to the polypeptide sequence selected from SEQ ID NO:2;

(f) an isolated polynucleotide comprising a polynucleotide sequence encoding the polypeptide selected from SEQ ID NO:2;

(g) an isolated polynucleotide having a polynucleotide sequence encoding a polypeptide sequence having at least 95%, 96%. 97%, 98%, or 99% identity to the polypeptide sequence selected from SEQ ID NO:2;

(h) an isolated polynucleotide encoding the polypeptide selected from SEQ ID NO:2;

(i) an isolated polynucleotide having or comprising a polynucleotide sequence that has an Identity Index of 0.95. 0.96, 0.97, 0.98, or 0.99 compared to the polynucleotide sequence selected from SEQ ID NO:1;

(j) an isolated polynucleotide having or comprising a polynucleotide sequence encoding a polypeptide sequence that has an Identity Index of 0.95, 0.96, 0.97. 0.98, or 0.99 compared to the polypeptide sequence selected from SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence selected from SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide selected from SEQ ID NO:2;

(b) is the RNA transcript of the DNA sequence encoding the polypeptide selected from SEQ ID NO:2;

(c) comprises an RNA transcript of the DNA sequence selected from SEQ ID NO:1; or (d) is the RNA transcript of the DNA sequence selected from SEQ ID NO:1;

and RNA polynucleotides that are complementary thereto.

The polynucleotide sequences of SEQ ID NO:1 show homology with E13203 (JP 1997149790-A), U75329 (Genomics 1997; 44:309–320). The polynucleotide sequencea of SEQ ID NO:1 are cDNA sequence that encode the polypeptides of SEQ ID NO:2. The polynucleotide sequencesencoding the polypeptides of SEQ ID NO:2 may be identical to the polypeptides encoding sequences of SEQ ID NO:1 or it may be a sequence other than SEQ ID NO:1, which, as a result of the redundancy (degeneracy) of the genetic code, also encodes the polypeptides of SEQ ID NO:2. The polypeptides of the SEQ ID NO:2 are related to other proteins of the serine protease family, having homology and/or structural similarity with pTMPRSS2 (Genomics 1997: 44:302–320).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one Seripancrin activity.

Polynucleotides of the present invention may be obtained using standard cloning and screening techniques from a cDNA library derived from mRNA in cells of human colon, colon tumour, pancreas, pancreas tumour, ovary 20 cancer, prostate cancer, pharynx carcinoma, adenocarcinoma, cheek carcinoma, squamous cell carcinoma, B-cell lymphoma, uterine cancer, testis, fetal lung and embryonic tissues. (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals ribosome binding sites and sequences that stabilize mRNA.

Polynucleotides that are identical, or have sufficient identity to a polynucleotide sequences selected from SEQ ID NO:1, may be used as hybridization probes for cDNA and genomic DNA or as primers for a nucleic 10 acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having a sequence selected from SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (l50mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having a sequence selected from SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example to those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology. (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterised by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Seripancrin nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising Seripancrin polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M.Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucteotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit comprising:
  (a) a polynucleotide of the present invention, preferably a nucleotide sequence of SEQ ID NO: 1, or a fragment or an RNA transcript thereof;
  (b) a nucleotide sequence complementary to that of (a);
  (c) a polypeptide of the present invention, preferably a polypeptide of SEQ ID NO:2 or a fragment thereof; or
  (d) an antibody to a polypeptide of the present invention, preferably to a polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiatiori Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar;5(3):339–46 A radiation hybrid map of the human genome. Gyapay G, Schmitt K. Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 11q22-q23 (D11S1347-D11S939).

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hydridisation techniques to clones arrayed on a grid, such as cDNA microarray hybridisation (Schena et al. Science. 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in colon, colon tumour, pancreas, pancreas tumour, ovary cancer, prostate cancer, pharynx carcinoma, adenocarcinoma, cheek carcinoma, squamous cell carcinoma, B-cell lymphoma, uterine cancer, testis, fetal lung and embryonic tissues.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C. Nature (1975) 256:495–497), the trioma technique, the human B-cell hybridoma technique (Kozbor et al.. Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands. receptors, enzymes, etc., as the case may be, of the polypeptide; a structural or functional mimetic thereof (see Coligan et al., Current Protocols in Immunology 1(2):Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a Seripancrin activity in the is mixture, and comparing the Seripancrin activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and Seripancrin polypeptide, as hereinbefore described, can also be used for 25 high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)). Screening techniques The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art: This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, 1251), chemically modified (for instance, biotinylated), or fused to a peptide sequence suitable for detection or purification, and incubated with a source of the putative receptor (cells, cell membranes, cell supernatants, tissue extracts, bodily fluids).

Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide. e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and Seripancrin gene. The art of constructing transgenic animals is well established. For example, the Seripancrin gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:
 (a) a polypeptide of the present invention;
 (b) a recombinant cell expressing a polypeptide of the present invention;
 (c) a cell membrane expressing a polypeptide of the present invention; or
 (d) an antibody to a polypeptide of the present invention; which polypeptide is preferably selected from SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an
Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules Is comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA, thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H.

Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging". Ann NY Acad Sci, 663, 48–62, 1992).

"Fragment" of a polypeptide sequence refers to a polypeptide sequence that is shorter than the reference sequence but that retains essentially the same biological function or activity as the reference polypeptide.

"Fragment" of a polynucleotide sequence refers to a polynucloetide sequence that is shorter than the reference sequences of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala: Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occuring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics. 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also know in the art, for instance the BLAST family of programs (Altschul S F et al. J Mol Biol, 215, 403–410, 1990 Altschul S F et al, Nucleic Acids res., 25:389–3402, 1997, available from the National Center for Biotechnology Information (NCBI), Bethesda, Md., USA and accessible through the home page of the NCBI at the world wide web at ncbi.nlm.nih.gov) and FASTA (Pearson W R, Methods in Enzymology, 183,63–99, 1990; Pearson W R and Lipman D J, Proc Nat Acad Sci USA, 85, 2444–2448, 1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a * I).$$

in which:

$n_a$ is the number of nucleotide or amino acid differences, $x_a$ is the total number of nucleotides or amino acids in SEQ ID NO:1 or SEQ ID NO:2. respectively, I is the Identity Index,

* is the symbol for the multiplication operator, and in which any non-integer product of Xa and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. No. 5,541,087, 5,726,044. In the case of Fc-Seripancrin, employing an immunoglobulin Fc region as a part of a fusion protein is advantageous for performing the functional expression of Fc-Seripancrin or fragments of -Seripancrin, to improve pharmacokinetic properties of such a fusion protein when used for therapy and to generate a dimeric Seripancrin. The to Fc-Seripancrin DNA construct comprises in 5' to 3' direction, a secretion cassette, i.e. a signal sequence that triggers export from a mammalian cell, DNA encoding an immunoglobulin Fc region fragment, as a fusion partner, and a DNA encoding Seripancrin or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

FURTHER EXAMPLES

Example 1

Construction of the baculovirus transfer vector and expression

DNA fragment encoding amino acid residues 52–435 of the main splicing isoform was cloned for expression of Seripancrin in the baculovirus expression system. For expression Stratagene's vector pPbac (Stratagene) was used.

This system allows expression of a secreted fusion protein where the signal peptide sequence of the human placental alkaline phosphatase protein is fused in front of the sequence to be expressed. The Seripancrin gene was introduced in frame in this vector via a 5' SmaI restriction site and a 3' BamHI side. A single PCR reaction was carried out using the 5' Primer: 5' AAC CCG GGA AAG GTG ATT CTG GAT AAA TAC TAC 3' and the 3' Primer: 5' AAGGATCC TTA CAG CTC AGC CTT CCA GAC ATT G 3' to amplify the above mentioned region of the main splicing isoform. To check for the maintenance of the correct open reading frame, the complete insert, the insert junctions and the signal peptide sequence provided by the vector was sequenced.

Expression of the fusion protein in Sf9 cells was done using standard laboratory methods for baculovirus systems based on expression from the polyhedron locus.

Additional variation of the Seripancrin sequence included in some cases the insertion of an $MRGS(H)_6$ tag at the 3'-end (C-Terminal) for easier detection of protein expression, purification and concentration.

Example 2

Production of Seripancrin

Culture supernatant containing Seripancrin was collected from the baculo expression system and concentrated by pressurized dialysis. A weak anion exchanger such as EMD-DEAE-Fractogel turned out to be ideal for a first adsorption of the protein. Desporption of seripancrin was done by using a linear sodium chloride gradient (0–0.8 M, NaCl, Tris, pH 7.5). Further purification depended mainly on the purity reached in this first chromatographic step. If necessary additional rechromatographies on ion exchanger supports have been conducted. The final step of purification was performed using a Superdex 75 column. The eluted samples have been collected and have been further concentrated by Centricon 10 centrifugation (Amicon) in PBS. These preparations have then been used to perform analytical as well as functional tests. For analytical grade purification of protein - necessary prior to protein sequencing—a reversed phase RP18 column has been used.

Optimization of the chromatographic conditions have been performed using a BiaCore chromatographic system with analytical columns available from Pharmacia. The BiaCore based separation protocol has been scaled up by using FPLC techniques. The optimized running conditions are directly convertible into a semi-preparative or preparative scale of separation. Samples collected from the last chromatographic step have been collected and analysed by SDS-PAGE. Protein bands have been visualized using Coomassie staining. Under reducing conditions the purified recombinant protein revealed a relative molecular weight of 55 kDA±2 kDa compared to the calculated theoretical molecular weight of 47962.

Isoelectric focussing using IEF-PAGE (Immobiline 3–10, Pharmacia) technique revealed an isolelectric point of pH 5.7±0.5. Protein bands and IEF-markers have been visualized using Coomassie staining In some cases a C-terminal histidin tagged version of the recombinant Seripancrin protein has been expressed. The expressed protein was detected by western blotting method using anti-MRGS(H)6 antibody. Purification was performed using chelators such as NTA or imido acetic acid immobilized on a column matrix and modified with metal ions such as Co, Ni, or Cu.

Example 3

Immunization and antibodies

With the purified recombinant protein available, immunization of animals has been started right away. Immune sera were raised in rabbits and high titered reagents were available for further screening.

Additional antisera have been generated by using synthetic peptides deduced from the sequence of the complete protein. Synthetic peptides have been synthesized (amino-acid sequence 15–28, 83–96, 166–180, 246–262, 382–395) coupled to KLH and used for immunization of rabbits. High titered immune sera generated with the recombinant protein or synthetic peptide have been used to established Elisa technology and Western blot technique to monitor and quantitate the recombinant protein. Generally antibodies of a given specificity have been pooled and precipitated with Ammonium-sulfat and dialysed against PBS. Selected sera have been biotinylated using the NHS-ester derivative of the biotin, available via Pierce. Biotinylation was performed according to the instruction of the manufacturer. The antigens and the immunochemical techniques used to raise and characterize the polyclonal antibodies can easily be combined with protocols used for the production of monoclonal antibody specificities. The expert in the field would make his choice between a classical technique such as the hybridoma based technology ore an antibody library based method according to his local possibilities.

Example 4

Immuno-Assays for estimation of Seripancrin

Specific sera raised with recombinant seripancrin have been used as a “catcher antibody” for the coating of 96-well micro-titer plates (Nunc). 50 μl of the anti-Seripancrin serum (20 μg/ml) has been used to coat plates over night. Prior to use, the plates have been washed three times with PBS and have been incubated for one hour with a BSA solution (1%) in order to prevent non-specific adhesion. Surplus of blocking solution has been removed and 50 μl Seripancrin has been added in serial delutions and has been incubated for one hour. Plates have been washed three times prior to the application of the biotinylated anti-Seripancrin antibody for detection. After an additional one hour, read-out has been performed via streptavidin-POD catalyzed colour reaction with substrates such as ODB-tablets (Dako) measured at 490 nm.

Example 5

Protease Activity Assay

To determine Seripancrin’s protease activity, recombinant secreted protein was purified from the supernatant of a baculovirus expression system expressing amino acid 52–435 of the main splicing isoform. The purified protein was added to a buffered solution containing a universal protease substrate (casein, resorufin-labeled; BOEHRINGER MANNHEIM) according to the manufacturer’s protocol.

What is claimed is:

1. An isolated seripancrin polypeptide which is:
   (a) an isolated polypeptide encoded by a polynucleotide comprising the sequence of SEQ ID NO:1; or
   (b) an isolated polypeptide comprising the amino acid sequence of SEQ ID NO:2.

2. The isolated polypeptide as claimed in claim 1, comprising the amino acid sequence of SEQ ID NO:2.

3. The isolated polypeptides as claimed in claim 1, consisting of the amino acid which is the polypeptide sequence of SEQ ID NO:2.

4. A fusion protein comprising an Immunoglobulin Fc-region and a polypeptide of claim 1.

5. An isolated polynucleotide which comprises:
   (a) a polynucleotide sequence encoding a polypeptide comprising the amino acid sequence of SEQ ID NO:2, or
   (b) the polynucleotide sequence of SEQ ID NO:1.

6. An isolated polynucleotide of claim 5, which comprises a polynucleotide sequence encoding a polypeptide comprising the amino acid sequence of SEQ ID NO:2.

7. An isolated polynucleotide of claim 5, which comprises the polynucleotide sequence of SEQ ID NO:1.

8. An expression vector comprising a polynucleotide of claim 7, wherein said expression vector is capable of producing the polypeptide encoded by said polynucleotide when present in a compatible host cell.

9. A recombinant host cell comprising the expression vector of claim 8.

10. An expression vector comprising a polynucleotide of claim 6, wherein said expression vector is capable of producing the polypeptide encoded by said polynucleotide when present in a compatible host cell.

11. A recombinant host cell comprising the expression vector of claim 10.

12. A process for producing a seripancrin polypeptide, comprising:
   culturing a host cell of claim 11 under conditions sufficient for the production of said polypeptide.

13. A process of claim 12, further comprising recovering the polypeptide from the culture medium.

14. A process for producing a seripancrin polypeptide, comprising:
   culturing a host cell of claim 9 under conditions sufficient for the production of said polypeptide.

15. A process of claim 9, further comprising recovering the polypeptide from the culture medium.

16. A method for screening to identify compounds that stimulate or inhibit the function or level of a seripancrin polypeptide of claim 1 comprising a method selected from the group consisting of:
   (a) measuring the binding of a candidate compound to the polypeptide (or to the cells or membranes expressing the polypeptide) or a fusion protein thereof;
   (b) measuring the competition of binding of a candidate compound to the polypeptide or a fusion protein thereof in the presence of a labeled competitor;
   (c) testing whether the candidate compound results in a signal generated by activation or inhibition of the polypeptide when expressed in a recombinant host cell;
   (d) mixing a candidate compound with a solution containing the polypeptide of claim 1, to form a mixture, measuring activity of the polypeptide in the mixture, and comparing the activity of the mixture to a control mixture which contains no candidate compound; or
   (e) detecting the effect of a candidate compound on the production of mRNA encoding said polypeptide or on said polypeptide in recombinant host cells, using an ELISA assay.

* * * * *

SEQUENCE LISTING

<160> NUMBER OF SEQ ID NOS: 6

<210> SEQ ID NO 1
<211> LENGTH: 1305
<212> TYPE: DNA
<213> ORGANISM: Homo sapiens
<220> FEATURE:
<221> NAME/KEY: CDS
<222> LOCATION: (1)..(1305)

<400> SEQUENCE: 1

```
atg gat cct gac agt gat caa cct ctg aac agc ctc gat gtc aaa ccc        48
Met Asp Pro Asp Ser Asp Gln Pro Leu Asn Ser Leu Asp Val Lys Pro
 1               5                  10                  15 ctg cgc aaa ccc cgt atc ccc atg gag acc ttc aga aag gtg ggg atc        96
Leu Arg Lys Pro Arg Ile Pro Met Glu Thr Phe Arg Lys Val Gly Ile
                 20                  25                  30 ccc atc atc ata gca cta ctg agc ctg gcg agt atc atc att gtg gtt       144
Pro Ile Ile Ile Ala Leu Leu Ser Leu Ala Ser Ile Ile Ile Val Val
             35                  40                  45 gtc ctc atc aag gtg att ctg gat aaa tac tac ttc ctc tgc ggg cag       192
Val Leu Ile Lys Val Ile Leu Asp Lys Tyr Tyr Phe Leu Cys Gly Gln
 50                  55                  60 cct ctc cac ttc atc ccg agg aag cag ctg tgt gac gga gag ctg gac       240
Pro Leu His Phe Ile Pro Arg Lys Gln Leu Cys Asp Gly Glu Leu Asp
 65                  70                  75                  80 tgt ccc ttg ggg gag gac gag gag cac tgt gtc aag agc ttc ccc gaa       288
Cys Pro Leu Gly Glu Asp Glu Glu His Cys Val Lys Ser Phe Pro Glu
                 85                  90                  95 ggg cct gca gtg gca gtc cgc ctc tcc aag gac cga tcc aca ctg cag       336
Gly Pro Ala Val Ala Val Arg Leu Ser Lys Asp Arg Ser Thr Leu Gln
            100                 105                 110 gtg ctg gac tcg gcc aca ggg aac tgg ttc tct gcc tgt ttc gac aac       384
Val Leu Asp Ser Ala Thr Gly Asn Trp Phe Ser Ala Cys Phe Asp Asn
        115                 120                 125 ttc aca gaa gct ctc gct gag aca gcc tgt agg cag atg ggc tac agc       432
Phe Thr Glu Ala Leu Ala Glu Thr Ala Cys Arg Gln Met Gly Tyr Ser
    130                 135                 140 agc aaa ccc act ttc aga gct gtg gag att ggc cca gac cag gat ctg       480
Ser Lys Pro Thr Phe Arg Ala Val Glu Ile Gly Pro Asp Gln Asp Leu
145                 150                 155                 160 gat gtt gtt gaa atc aca gaa aac agc cag gag ctt cgc atg cgg aac       528
Asp Val Val Glu Ile Thr Glu Asn Ser Gln Glu Leu Arg Met Arg Asn
                165                 170                 175 tca agt ggg ccc tgt ctc tca ggc tcc ctg gtc tcc ctg cac tgt ctt       576
Ser Ser Gly Pro Cys Leu Ser Gly Ser Leu Val Ser Leu His Cys Leu
            180                 185                 190 gcc tgt ggg aag agc ctg aag acc ccc cgt gtg gtg ggt ggg gag gag       624
Ala Cys Gly Lys Ser Leu Lys Thr Pro Arg Val Val Gly Gly Glu Glu
        195                 200                 205 gcc tct gtg gat tct tgg cct tgg cag gtc agc atc cag tac gac aaa       672
Ala Ser Val Asp Ser Trp Pro Trp Gln Val Ser Ile Gln Tyr Asp Lys
    210                 215                 220 cag cac gtc tgt gga ggg agc atc ctg gac ccc cac tgg gtc ctc acg       720
Gln His Val Cys Gly Gly Ser Ile Leu Asp Pro His Trp Val Leu Thr
225                 230                 235                 240 gca gcc cac tgc ttc agg aaa cat acc gat gtg ttc aac tgg aag gtg       768
Ala Ala His Cys Phe Arg Lys His Thr Asp Val Phe Asn Trp Lys Val
                245                 250                 255
```

| | | |
|---|---|---|
| cgg gca ggc tca gac aaa ctg ggc agc ttc cca tcc ctg gct gtg gcc<br>Arg Ala Gly Ser Asp Lys Leu Gly Ser Phe Pro Ser Leu Ala Val Ala<br>260                            265                        270 | | 816 |
| aag atc atc atc att gaa ttc aac ccc atg tac ccc aaa gac aat gac<br>Lys Ile Ile Ile Ile Glu Phe Asn Pro Met Tyr Pro Lys Asp Asn Asp<br>275                           280                        285 | | 864 |
| atc gcc ctc atg aag ctg cag ttc cca ctc act ttc tca ggc aca gtc<br>Ile Ala Leu Met Lys Leu Gln Phe Pro Leu Thr Phe Ser Gly Thr Val<br>290                          295                       300 | | 912 |
| agg ccc atc tgt ctg ccc ttc ttt gat gag gag ctc act cca gcc acc<br>Arg Pro Ile Cys Leu Pro Phe Phe Asp Glu Glu Leu Thr Pro Ala Thr<br>305                       310                   315                   320 | | 960 |
| cca ctc tgg atc att gga tgg ggc ttt acg aag cag aat gga ggg aag<br>Pro Leu Trp Ile Ile Gly Trp Gly Phe Thr Lys Gln Asn Gly Gly Lys<br>                        325                       330                   335 | | 1008 |
| atg tct gac ata ctg ctg cag gcg tca gtc cag gtc att gac agc aca<br>Met Ser Asp Ile Leu Leu Gln Ala Ser Val Gln Val Ile Asp Ser Thr<br>                 340                       345                       350 | | 1056 |
| cgg tgc aat gca gac gat gcg tac cag ggg gaa gtc acc gag aag atg<br>Arg Cys Asn Ala Asp Asp Ala Tyr Gln Gly Glu Val Thr Glu Lys Met<br>               355                       360                       365 | | 1104 |
| atg tgt gca ggc atc ccg gaa ggg ggt gtg gac acc tgc cag ggt gac<br>Met Cys Ala Gly Ile Pro Glu Gly Gly Val Asp Thr Cys Gln Gly Asp<br>370                          375                       380 | | 1152 |
| agt ggt ggg ccc ctg atg tac caa tct gac cag tgg cat gtg gtg ggc<br>Ser Gly Gly Pro Leu Met Tyr Gln Ser Asp Gln Trp His Val Val Gly<br>385                          390                       395                   400 | | 1200 |
| atc gtt agc tgg ggc tat ggc tgc ggg ggc ccg agc acc cca gga gta<br>Ile Val Ser Trp Gly Tyr Gly Cys Gly Gly Pro Ser Thr Pro Gly Val<br>                        405                       410                   415 | | 1248 |
| tac acc aag gtc tca gcc tat ctc aac tgg atc tac aat gtc tgg aag<br>Tyr Thr Lys Val Ser Ala Tyr Leu Asn Trp Ile Tyr Asn Val Trp Lys<br>                 420                       425                   430 | | 1296 |
| gct gag ctg<br>Ala Glu Leu<br>               435 | | 1305 |

<210> SEQ ID NO 2
<211> LENGTH: 435
<212> TYPE: PRT
<213> ORGANISM: Homo sapiens

<400> SEQUENCE: 2

Met Asp Pro Asp Ser Asp Gln Pro Leu Asn Ser Leu Asp Val Lys Pro
 1               5                  10                  15

Leu Arg Lys Pro Arg Ile Pro Met Glu Thr Phe Arg Lys Val Gly Ile
            20                  25                  30

Pro Ile Ile Ile Ala Leu Leu Ser Leu Ala Ser Ile Ile Ile Val Val
        35                  40                  45

Val Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

```
Phe Thr Glu Ala Leu Ala Glu Thr Ala Cys Arg Gln Met Gly Tyr Ser
    130                 135                 140
Ser Lys Pro Thr Phe Arg Ala Val Glu Ile Gly Pro Asp Gln Asp Leu
145                 150                 155                 160
Asp Val Glu Ile Thr Glu Asn Ser Gln Glu Leu Arg Met Arg Asn
                165                 170                 175
Ser Ser Gly Pro Cys Leu Ser Gly Ser Leu Val Ser Leu His Cys Leu
                180                 185                 190
Ala Cys Gly Lys Ser Leu Lys Thr Pro Arg Val Val Gly Gly Glu Glu
            195                 200                 205
Ala Ser Val Asp Ser Trp Pro Trp Gln Val Ser Ile Gln Tyr Asp Lys
    210                 215                 220
Gln His Val Cys Gly Gly Ser Ile Leu Asp Pro His Trp Val Leu Thr
225                 230                 235                 240
Ala Ala His Cys Phe Arg Lys His Thr Asp Val Phe Asn Trp Lys Val
                245                 250                 255
Arg Ala Gly Ser Asp Lys Leu Gly Ser Phe Pro Ser Leu Ala Val Ala
                260                 265                 270
Lys Ile Ile Ile Ile Glu Phe Asn Pro Met Tyr Pro Lys Asp Asn Asp
            275                 280                 285
Ile Ala Leu Met Lys Leu Gln Phe Pro Leu Thr Phe Ser Gly Thr Val
    290                 295                 300
Arg Pro Ile Cys Leu Pro Phe Phe Asp Glu Glu Leu Thr Pro Ala Thr
305                 310                 315                 320
Pro Leu Trp Ile Ile Gly Trp Gly Phe Thr Lys Gln Asn Gly Gly Lys
                325                 330                 335
Met Ser Asp Ile Leu Leu Gln Ala Ser Val Gln Val Ile Asp Ser Thr
                340                 345                 350
Arg Cys Asn Ala Asp Asp Ala Tyr Gln Gly Glu Val Thr Glu Lys Met
            355                 360                 365
Met Cys Ala Gly Ile Pro Glu Gly Gly Val Asp Thr Cys Gln Gly Asp
    370                 375                 380
Ser Gly Gly Pro Leu Met Tyr Gln Ser Asp Gln Trp His Val Val Gly
385                 390                 395                 400
Ile Val Ser Trp Gly Tyr Gly Cys Gly Gly Pro Ser Thr Pro Gly Val
                405                 410                 415
Tyr Thr Lys Val Ser Ala Tyr Leu Asn Trp Ile Tyr Asn Val Trp Lys
            420                 425                 430
Ala Glu Leu
        435
```

<210> SEQ ID NO 3
<211> LENGTH: 1479
<212> TYPE: DNA
<213> ORGANISM: Homo sapiens
<220> FEATURE:
<221> NAME/KEY: CDS
<222> LOCATION: (1)..(1479)

<400> SEQUENCE: 3

```
atg gat cct gac agt gat caa cct ctg aac agc ctc gat gtc aaa ccc    48
Met Asp Pro Asp Ser Asp Gln Pro Leu Asn Ser Leu Asp Val Lys Pro
  1               5                  10                  15 ctg cgc aaa ccc cgt atc ccc atg gag acc ttc aga aag gtg ggg atc    96
Leu Arg Lys Pro Arg Ile Pro Met Glu Thr Phe Arg Lys Val Gly Ile
             20                  25                  30
```

| | |
|---|---|
| ccc atc atc ata gca cta ctg agc ctg gcg agt atc atc att gtg gtt<br>Pro Ile Ile Ile Ala Leu Leu Ser Leu Ala Ser Ile Ile Ile Val Val<br>                35                          40                        45 | 144 |
| gtc ctc atc aag gtg att ctg gat aaa tac tac ttc ctc tgc ggg cag<br>Val Leu Ile Lys Val Ile Leu Asp Lys Tyr Tyr Phe Leu Cys Gly Gln<br>     50                          55                          60 | 192 |
| cct ctc cac ttc atc ccg agg aag cag ctg tgt gac gga gag ctg gac<br>Pro Leu His Phe Ile Pro Arg Lys Gln Leu Cys Asp Gly Glu Leu Asp<br>65                         70                          75                          80 | 240 |
| tgt ccc ttg ggg gag gac gag gag cac tgt gtc aag agc ttc ccc gaa<br>Cys Pro Leu Gly Glu Asp Glu Glu His Cys Val Lys Ser Phe Pro Glu<br>                          85                          90                          95 | 288 |
| ggg cct gca gtg gca gtc cgc ctc tcc aag gac cga tcc aca ctg cag<br>Gly Pro Ala Val Ala Val Arg Leu Ser Lys Asp Arg Ser Thr Leu Gln<br>                100                        105                       110 | 336 |
| gtg ctg gac tcg gcc aca ggg aac tgg ttc tct gcc tgt ttc gac aac<br>Val Leu Asp Ser Ala Thr Gly Asn Trp Phe Ser Ala Cys Phe Asp Asn<br>     115                         120                       125 | 384 |
| ttc aca gaa gct ctc gct gag aca gcc tgt agg cag atg ggc tac agc<br>Phe Thr Glu Ala Leu Ala Glu Thr Ala Cys Arg Gln Met Gly Tyr Ser<br>     130                         135                       140 | 432 |
| agc aaa ccc act ttc aga gct gtg gag att ggc cca gac cag gat ctg<br>Ser Lys Pro Thr Phe Arg Ala Val Glu Ile Gly Pro Asp Gln Asp Leu<br>145                       150                       155                       160 | 480 |
| gat gtt gtt gaa atc aca gaa aac agc cag gag ctt cgc atg cgg aac<br>Asp Val Val Glu Ile Thr Glu Asn Ser Gln Glu Leu Arg Met Arg Asn<br>                165                        170                       175 | 528 |
| tca agt ggg ccc tgt ctc tca ggc tcc ctg gtc tcc ctg cac tgt ctt<br>Ser Ser Gly Pro Cys Leu Ser Gly Ser Leu Val Ser Leu His Cys Leu<br>                    180                        185                       190 | 576 |
| gcc tgt ggg aag agc ctg aag acc ccc cgt gtg gtg ggt ggg gag gag<br>Ala Cys Gly Lys Ser Leu Lys Thr Pro Arg Val Val Gly Gly Glu Glu<br>     195                         200                       205 | 624 |
| gcc tct gtg gat tct tgg cct tgg cag gtc agc atc cag tac gac aaa<br>Ala Ser Val Asp Ser Trp Pro Trp Gln Val Ser Ile Gln Tyr Asp Lys<br>     210                         215                       220 | 672 |
| cag cac gtc tgt gga ggg agc atc ctg gac ccc cac tgg gtc ctc acg<br>Gln His Val Cys Gly Gly Ser Ile Leu Asp Pro His Trp Val Leu Thr<br>225                       230                       235                       240 | 720 |
| gca gcc cac tgc ttc agg aaa cat acc gat gtg ttc aac tgg aag gtg<br>Ala Ala His Cys Phe Arg Lys His Thr Asp Val Phe Asn Trp Lys Val<br>                245                       250                       255 | 768 |
| cgg gca ggc tca gac aaa ctg ggc agc ttc cca tcc ctg gct gtg gcc<br>Arg Ala Gly Ser Asp Lys Leu Gly Ser Phe Pro Ser Leu Ala Val Ala<br>                260                       265                       270 | 816 |
| aag atc atc atc att gaa ttc aac ccc atg tac ccc aaa gac aat gac<br>Lys Ile Ile Ile Ile Glu Phe Asn Pro Met Tyr Pro Lys Asp Asn Asp<br>     275                         280                       285 | 864 |
| atc gcc ctc atg aag ctg cag ttc cca ctc act ttc tca ggc aca gtc<br>Ile Ala Leu Met Lys Leu Gln Phe Pro Leu Thr Phe Ser Gly Thr Val<br>     290                         295                       300 | 912 |
| agg ccc atc tgt ctg ccc ttc ttt gat gag gag ctc act cca gcc acc<br>Arg Pro Ile Cys Leu Pro Phe Phe Asp Glu Glu Leu Thr Pro Ala Thr<br>305                       310                       315                       320 | 960 |
| cca ctc tgg atc att gga tgg ggc ttt acg aag cag aat gga ggg aag<br>Pro Leu Trp Ile Ile Gly Trp Gly Phe Thr Lys Gln Asn Gly Gly Lys<br>                325                       330                       335 | 1008 |
| atg tct gac ata ctg ctg cag gcg tca gtc cag gtc att gac agc aca<br>Met Ser Asp Ile Leu Leu Gln Ala Ser Val Gln Val Ile Asp Ser Thr<br>                    340                        345                       350 | 1056 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cgg | tgc | aat | gca | gac | gat | gcg | tac | cag | ggg | gaa | gtc | acc | gag | aag | atg | 1104 |
| Arg | Cys | Asn | Ala | Asp | Asp | Ala | Tyr | Gln | Gly | Glu | Val | Thr | Glu | Lys | Met |      |
|     | 355 |     |     |     |     | 360 |     |     |     |     | 365 |     |     |     |     |      |
| atg | tgt | gca | ggc | atc | ccg | gaa | ggg | ggt | gtg | gac | acc | tgc | cag | ggt | gac | 1152 |
| Met | Cys | Ala | Gly | Ile | Pro | Glu | Gly | Gly | Val | Asp | Thr | Cys | Gln | Gly | Asp |      |
| 370 |     |     |     |     | 375 |     |     |     |     | 380 |     |     |     |     |     |      |
| agt | ggt | ggg | ccc | ctg | atg | tac | caa | tct | gac | cag | tgg | cat | gtg | gtg | ggc | 1200 |
| Ser | Gly | Gly | Pro | Leu | Met | Tyr | Gln | Ser | Asp | Gln | Trp | His | Val | Val | Gly |      |
| 385 |     |     |     |     | 390 |     |     |     |     | 395 |     |     |     |     | 400 |      |
| atc | gtt | agc | tgg | ggc | tat | ggc | tgc | ggg | ggc | ccg | agc | acc | cca | gga | gta | 1248 |
| Ile | Val | Ser | Trp | Gly | Tyr | Gly | Cys | Gly | Gly | Pro | Ser | Thr | Pro | Gly | Val |      |
|     |     |     |     | 405 |     |     |     |     | 410 |     |     |     |     | 415 |     |      |
| tac | acc | aag | gtc | tca | gcc | tat | ctc | aac | tgg | atc | tac | aat | gtc | tgg | aag | 1296 |
| Tyr | Thr | Lys | Val | Ser | Ala | Tyr | Leu | Asn | Trp | Ile | Tyr | Asn | Val | Trp | Lys |      |
|     |     « 420 |     |     |     |     | 425 |     |     |     |     | 430 |     |     |     |      |
| gat | aga | act | att | cag | aga | agc | tgt | aac | tcc | cca | ggg | aca | ggt | ctt | gtg | 1344 |
| Asp | Arg | Thr | Ile | Gln | Arg | Ser | Cys | Asn | Ser | Pro | Gly | Thr | Gly | Leu | Val |      |
|     |     |     |     | 435 |     |     |     |     | 440 |     |     |     |     | 445 |     |      |
| att | cag | caa | cca | gct | gta | ccg | ctg | atg | gag | cta | cgg | tca | gct | cgg | cac | 1392 |
| Ile | Gln | Gln | Pro | Ala | Val | Pro | Leu | Met | Glu | Leu | Arg | Ser | Ala | Arg | His |      |
|     | 450 |     |     |     |     | 455 |     |     |     |     | 460 |     |     |     |     |      |
| aca | cat | cgc | ctg | acc | acc | tgt | gtt | tgc | ttt | ctc | tca | ttc | cct | gcc | tta | 1440 |
| Thr | His | Arg | Leu | Thr | Thr | Cys | Val | Cys | Phe | Leu | Ser | Phe | Pro | Ala | Leu |      |
| 465 |     |     |     |     | 470 |     |     |     |     | 475 |     |     |     |     | 480 |      |
| cag | ccc | ctg | tcc | ccc | tta | tgc | cca | ttt | ccc | tgg | gat | tga |     |     |     | 1479 |
| Gln | Pro | Leu | Ser | Pro | Leu | Cys | Pro | Phe | Pro | Trp | Asp |     |     |     |     |      |
|     |     |     | 485 |     |     |     |     | 490 |     |     |     |     |     |     |     |      |

<210> SEQ ID NO 4
<211> LENGTH: 492
<212> TYPE: PRT
<213> ORGANISM: Homo sapiens

<400> SEQUENCE: 4

Met Asp Pro Asp Ser Asp Gln Pro Leu Asn Ser Leu Asp Val Lys Pro
1               5                   10                  15

Leu Arg Lys Pro Arg Ile Pro Met Glu Thr Phe Arg Lys Val Gly Ile
                20                  25                  30

Pro Ile Ile Ile Ala Leu Leu Ser Leu Ala Ser Ile Ile Val Val
            35                  40                  45

Val Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

```
Ala Cys Gly Lys Ser Leu Lys Thr Pro Arg Val Val Gly Glu Glu
            195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Ile Glu Phe Asn Pro Met Tyr Pro Lys Asp Asn Asp
        275                 280                 285

Ile Ala Leu Met Lys Leu Gln Phe Pro Leu Thr Phe Ser Gly Thr Val
    290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
            420                 425                 430

Asp Arg Thr Ile Gln Arg Ser Cys Asn Ser Pro Gly Thr Gly Leu Val
        435                 440                 445

Ile Gln Gln Pro Ala Val Pro Leu Met Glu Leu Arg Ser Ala Arg His
    450                 455                 460

Thr His Arg Leu Thr Thr Cys Val Cys Phe Leu Ser Phe Pro Ala Leu
465                 470                 475                 480

Gln Pro Leu Ser Pro Leu Cys Pro Phe Pro Trp Asp
                485                 490
```

<210> SEQ ID NO 5
<211> LENGTH: 609
<212> TYPE: DNA
<213> ORGANISM: Homo sapiens
<220> FEATURE:
<221> NAME/KEY: CDS
<222> LOCATION: (1)..(609)

<400> SEQUENCE: 5

```
atg gat cct gac agt gat caa cct ctg aac agc ctc gat gtc aaa ccc      48
Met Asp Pro Asp Ser Asp Gln Pro Leu Asn Ser Leu Asp Val Lys Pro
  1               5                  10                  15 ctg cgc aaa ccc cgt atc ccc atg gag acc ttc aga aag gtg ggg atc      96
Leu Arg Lys Pro Arg Ile Pro Met Glu Thr Phe Arg Lys Val Gly Ile
              20                  25                  30 ccc atc atc ata gca cta ctg agc ctg gcg agt atc atc att gtg gtt     144
Pro Ile Ile Ile Ala Leu Leu Ser Leu Ala Ser Ile Ile Ile Val Val
          35                  40                  45
```

```
gtc ctc atc aag gtg att ctg gat aaa tac tac ttc ctc tgc ggg cag      192
Val Leu Ile Lys Val Ile Leu Asp Lys Tyr Tyr Phe Leu Cys Gly Gln
     50                  55                  60 cct ctc cac ttc atc ccg agg aag cag ctg tgt gac gga gag ctg gac      240
Pro Leu His Phe Ile Pro Arg Lys Gln Leu Cys Asp Gly Glu Leu Asp
 65                  70                  75                  80 tgt ccc ttg ggg gag gac gag gag cac tgt gtc aag agc ttc ccc gaa      288
Cys Pro Leu Gly Glu Asp Glu Glu His Cys Val Lys Ser Phe Pro Glu
                 85                  90                  95 ggg cct gca gtg gca gtc cgc ctc tcc aag gac cga tcc aca ctg cag      336
Gly Pro Ala Val Ala Val Arg Leu Ser Lys Asp Arg Ser Thr Leu Gln
            100                 105                 110 gtg ctg gac tcg gcc aca ggg aac tgg ttc tct gcc tgt ttc gac aac      384
Val Leu Asp Ser Ala Thr Gly Asn Trp Phe Ser Ala Cys Phe Asp Asn
        115                 120                 125 ttc aca gca gcc cta gct cgg cca cac ttg gtg ctc cca gca tcc cag      432
Phe Thr Ala Ala Leu Ala Arg Pro His Leu Val Leu Pro Ala Ser Gln
    130                 135                 140 gga gag aca cag ccc act gaa caa ggt ctc agg ggt att gct aag cca      480
Gly Glu Thr Gln Pro Thr Glu Gln Gly Leu Arg Gly Ile Ala Lys Pro
145                 150                 155                 160 aga agg aac ttt ccc aca cta ctg aat gga agc agg ctg tct tgt aaa      528
Arg Arg Asn Phe Pro Thr Leu Leu Asn Gly Ser Arg Leu Ser Cys Lys
                165                 170                 175 agc cca gat cac tgt ggg ctg gag agg aga agg aaa ggg tct gcg cca      576
Ser Pro Asp His Cys Gly Leu Glu Arg Arg Arg Lys Gly Ser Ala Pro
            180                 185                 190 gcc ctg tcc gtc ttc acc cat ccc caa gcc tac                          609
Ala Leu Ser Val Phe Thr His Pro Gln Ala Tyr
        195                 200

<210> SEQ ID NO 6
<211> LENGTH: 203
<212> TYPE: PRT
<213> ORGANISM: Homo sapiens

<400> SEQUENCE: 6

Met Asp Pro Asp Ser Asp Gln Pro Leu Asn Ser Leu Asp Val Lys Pro
 1               5                  10                  15

Leu Arg Lys Pro Arg Ile Pro Met Glu Thr Phe Arg Lys Val Gly Ile
                20                  25                  30

Pro Ile Ile Ile Ala Leu Leu Ser Leu Ala Ser Ile Ile Val Val
            35                  40                  45

Val Leu Ile Lys Val Ile Leu Asp Lys Tyr Tyr Phe Leu Cys Gly Gln
     50                  55                  60

Pro Leu His Phe Ile Pro Arg Lys Gln Leu Cys Asp Gly Glu Leu Asp
 65                  70                  75                  80

Cys Pro Leu Gly Glu Asp Glu Glu His Cys Val Lys Ser Phe Pro Glu
                 85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Ala Ala Leu Ala Arg Pro His Leu Val Leu Pro Ala Ser Gln
    130                 135                 140

Gly Glu Thr Gln Pro Thr Glu Gln Gly Leu Arg Gly Ile Ala Lys Pro
145                 150                 155                 160
```

-continued

```
Arg Arg Asn Phe Pro Thr Leu Leu Asn Gly Ser Arg Leu Ser Cys Lys
            165                 170                 175

Ser Pro Asp His Cys Gly Leu Glu Arg Arg Arg Lys Gly Ser Ala Pro
            180                 185                 190

Ala Leu Ser Val Phe Thr His Pro Gln Ala Tyr
            195             200
```